(12) United States Patent
Sainz de Cea et al.

(10) Patent No.: US 11,132,793 B2
(45) Date of Patent: Sep. 28, 2021

(54) CASE-ADAPTIVE MEDICAL IMAGE QUALITY ASSESSMENT

(71) Applicant: INTERNATIONAL BUSINESS MACHINES CORPORATION, Armonk, NY (US)

(72) Inventors: Maria Victoria Sainz de Cea, Somerville, MA (US); David Richmond, Newton, MA (US)

(73) Assignee: International Business Machines Corporation, Armonk, NY (US)

( * ) Notice: Subject to any disclaimer, the term of this patent is extended or adjusted under 35 U.S.C. 154(b) by 117 days.

(21) Appl. No.: 16/528,731

(22) Filed: Aug. 1, 2019

(65) Prior Publication Data

US 2021/0035285 A1 Feb. 4, 2021

(51) Int. Cl.
| | |
|---|---|
| G06T 7/00 | (2017.01) |
| G06T 7/11 | (2017.01) |
| G06K 9/03 | (2006.01) |
| G06K 9/46 | (2006.01) |
| G06N 3/08 | (2006.01) |
| G06K 9/62 | (2006.01) |
| G16H 30/20 | (2018.01) |

(52) U.S. Cl.
CPC ............ *G06T 7/0012* (2013.01); *G06K 9/036* (2013.01); *G06K 9/4604* (2013.01); *G06N 3/08* (2013.01);
(Continued)

(58) Field of Classification Search
CPC .... G06K 9/036; G06K 9/4604; G06K 9/6262; G06K 9/6269; G06N 3/08;
(Continued)

(56) References Cited

U.S. PATENT DOCUMENTS

| | | |
|---|---|---|
| 7,865,002 B2 | 1/2011 | Basilico et al. |
| 9,740,710 B2 | 8/2017 | Han et al. |

(Continued)

FOREIGN PATENT DOCUMENTS

| | | |
|---|---|---|
| CN | 105354835 A | 2/2016 |
| CN | 108109145 A | 6/2018 |

OTHER PUBLICATIONS

Kuang et al., "FAIM—A ConvNet Method for Unsupervised 3D Medical Image Registration", 9 pages, Nov. 22, 2018, arXiv:1811.09243v1 [cs.CV].

(Continued)

*Primary Examiner* — Kim Y Vu
*Assistant Examiner* — Francisco A Agra
(74) *Attorney, Agent, or Firm* — Rakesh Roy

(57) ABSTRACT

A method, computer system, and a computer program product for case-adaptive image quality assessment is provided. The present invention may include detecting a current set of features in a current exam associated with a patient. The present invention may also include calculating a current set of quality measurements for the current exam based on the detected current set of features. The present invention may further include in response to determining that the calculated current set of quality measurements for the current exam is below a patient-specific image quality threshold defined by at least one prior exam associated with the patient, automatically registering a negative quality assessment for the current exam associated with the patient.

17 Claims, 8 Drawing Sheets

(52) U.S. Cl.
CPC .............. *G06T 7/11* (2017.01); *G06K 9/6262* (2013.01); *G06K 9/6269* (2013.01); *G06T 2207/10081* (2013.01); *G06T 2207/10116* (2013.01); *G06T 2207/30068* (2013.01); *G06T 2207/30168* (2013.01); *G16H 30/20* (2018.01)

(58) Field of Classification Search
CPC . G06T 2207/10081; G06T 2207/10116; G06T 2207/30068; G06T 2207/30168; G06T 7/0012; G06T 7/11; G16H 30/20
See application file for complete search history.

(56) References Cited

U.S. PATENT DOCUMENTS

| | | | | |
|---|---|---|---|---|
| 2006/0274145 | A1* | 12/2006 | Reiner | G16H 30/20 348/62 |
| 2007/0086641 | A1* | 4/2007 | Nakamura | G06T 7/0012 382/132 |
| 2011/0123087 | A1* | 5/2011 | Nie | G06T 7/62 382/132 |
| 2014/0056502 | A1* | 2/2014 | Twellmann | G06T 7/0014 382/131 |
| 2017/0065238 | A1* | 3/2017 | Smith | A61B 8/0825 |
| 2019/0026608 | A1 | 1/2019 | Hsieh et al. | |
| 2019/0156477 | A1* | 5/2019 | Perrin | G16H 30/40 |
| 2019/0287241 | A1* | 9/2019 | Hill | A61B 6/5217 |
| 2020/0250814 | A1* | 8/2020 | Stoval, III | G06N 20/00 |

OTHER PUBLICATIONS

Volpara Solutions, "Volpara® enterprise", Volpara Solutions—EQUIP with VolparaEnterprise, Accessed on Jul. 30, 2019, 5 pages.
Mell et al., "The NIST Definition of Cloud Computing", Recommendations of the National Institute of Standards and Technology, Special Publication 800-145, Sep. 2011, 7 pages.

* cited by examiner

CASE-ADAPTIVE MEDICAL IMAGE QUALITY ASSESSMENT

BACKGROUND

The present invention relates generally to the field of computing, and more particularly to computer-aided diagnosis.

Patient medical imaging studies are often conducted as part of diagnostic decision making and treatments. Typically, a physician, such as a radiologist, may analyze a medical image and interpret the findings observed in the medical image. More recently, artificial intelligence (AI) techniques have been implemented to enable medical imaging and analysis without significant human intervention.

SUMMARY

Embodiments of the present invention disclose a method, computer system, and a computer program product for case-adaptive image quality assessment. The present invention may include detecting a current set of features in a current exam associated with a patient. The present invention may also include calculating a current set of quality measurements for the current exam based on the detected current set of features. The present invention may further include in response to determining that the calculated current set of quality measurements for the current exam is below a patient-specific image quality threshold defined by at least one prior exam associated with the patient, automatically registering a negative quality assessment for the current exam associated with the patient.

BRIEF DESCRIPTION OF THE SEVERAL VIEWS OF THE DRAWINGS

These and other objects, features and advantages of the present invention will become apparent from the following detailed description of illustrative embodiments thereof, which is to be read in connection with the accompanying drawings. The various features of the drawings are not to scale as the illustrations are for clarity in facilitating one skilled in the art in understanding the invention in conjunction with the detailed description. In the drawings.

DETAILED DESCRIPTION

Figure 1:
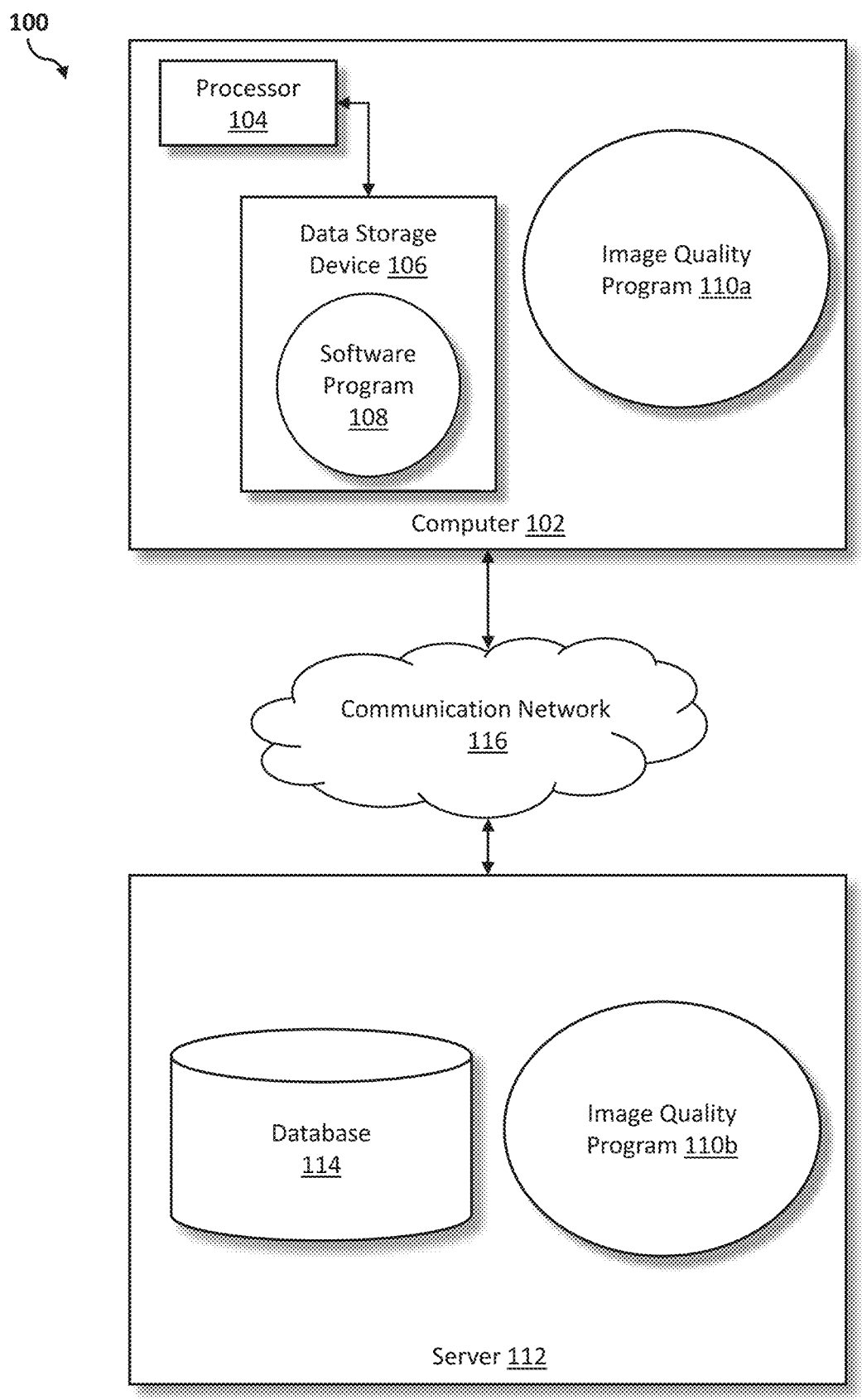
FIG. 1 illustrates a networked computer environment according to at least one embodiment.

Detailed embodiments of the claimed structures and methods are disclosed herein; however, it can be understood that the disclosed embodiments are merely illustrative of the claimed structures and methods that may be embodied in various forms. This invention may, however, be embodied in many different forms and should not be construed as limited to the exemplary embodiments set forth herein. Rather, these exemplary embodiments are provided so that this disclosure will be thorough and complete and will fully convey the scope of this invention to those skilled in the art. In the description, details of well-known features and techniques may be omitted to avoid unnecessarily obscuring the presented embodiments.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language, Python programming language, or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The following described exemplary embodiments provide a system, method and program product for case-adaptive (e.g., patient-specific) medical image quality assessment. As such, the present embodiment has the capacity to improve the technical field of computer-aided diagnosis (CAD) by automatically determining whether a medical image in a current exam includes sufficient image quality for medical use (e.g., clinical image analysis). More specifically, an image quality program may calculate a first or prior set of quality measurements based on one or more prior exams and a second or current set of quality measurements based on a current exam. The image quality program may then compare the current set of quality measurements with the prior set of quality measurements to determine if a quality assessment of the current exam is lower than a quality assessment of the prior exams. If the image quality program determines that the quality assessment of the current exam is not lower than the quality assessment of the prior exams, the image quality program may automatically register a positive quality assessment for the current exam and process the current exam for analysis by a CAD device. However, if the image quality program determines that the quality assessment of the current exam is lower than the quality assessment of the prior exams, the image quality program may automatically register a negative quality assessment for the current exam (e.g., flag the current exam as including low image quality).

As described previously, patient medical imaging studies are often conducted as part of diagnostic decision making and treatments. Typically, a physician, such as a radiologist, may analyze a medical image and interpret the findings observed in the medical image. More recently, artificial intelligence (AI) techniques have been implemented to enable medical imaging and analysis without significant human intervention. Before analyzing a medical image for diagnostic interpretation, a physician may typically assess the quality of the medical image to determine whether the medical image meets one or more image quality criteria. A similar quality assessment of the medical images may be necessary prior to diagnostic interpretation using a CAD device. If low quality medical images are analyzed using CAD devices, the diagnostic interpretation may be unreliable and result in increased false positive detection of suspicious findings.

Therefore, it may be advantageous to, among other things, provide a way to automatically assess the quality of the medical image to determine whether the medical image meets one or more image quality criteria, prior to diagnostic interpretation of the medical image by a CAD device. It may also be advantageous to among other things, provide a way to measure a patient-specific quality assessment of the medical image. Specifically, it may be advantageous to use prior exams of a given patient to establish a patient-specific image quality threshold which may incorporate one or more characteristics (e.g., anatomy, habitus, mobility). Thereafter, if a current exam falls below the patient-specific image quality threshold, the low quality of the medical image may be determined to be a result of imaging procedure error.

Referring to FIG. 1, an exemplary networked computer environment 100 in accordance with one embodiment is depicted. The networked computer environment 100 may include a computer 102 with a processor 104 and a data storage device 106 that is enabled to run a software program 108 and an image quality program 110a. The networked computer environment 100 may also include a server 112 that is enabled to run an image quality program 110b that may interact with a database 114 and a communication network 116. The networked computer environment 100 may include a plurality of computers 102 and servers 112, only one of which is shown. The communication network 116 may include various types of communication networks, such as a wide area network (WAN), local area network (LAN), a telecommunication network, a wireless network, a public switched network and/or a satellite network. It should be appreciated that FIG. 1 provides only an illustration of one implementation and does not imply any limitations with regard to the environments in which different embodiments may be implemented. Many modifications to the depicted environments may be made based on design and implementation requirements.

The client computer 102 may communicate with the server computer 112 via the communications network 116. The communications network 116 may include connections, such as wire, wireless communication links, or fiber optic cables. As will be discussed with reference to FIG. 6, server computer 112 may include internal components 902a and external components 904a, respectively, and client computer 102 may include internal components 902b and external components 904b, respectively. Server computer 112 may also operate in a cloud computing service model, such as Software as a Service (SaaS), Platform as a Service (PaaS), or Infrastructure as a Service (IaaS). Server 112 may also be located in a cloud computing deployment model, such as a private cloud, community cloud, public cloud, or hybrid cloud. Client computer 102 may be, for example, a mobile device, a telephone, a personal digital assistant, a netbook, a laptop computer, a tablet computer, a desktop computer, or any type of computing devices capable of running a program, accessing a network, and accessing a database 114. According to various implementations of the present embodiment, the image quality program 110a, 110b may interact with a database 114 that may be embedded in various storage devices, such as, but not limited to a computer/mobile device 102, a networked server 112, or a cloud storage service.

Figure 2:
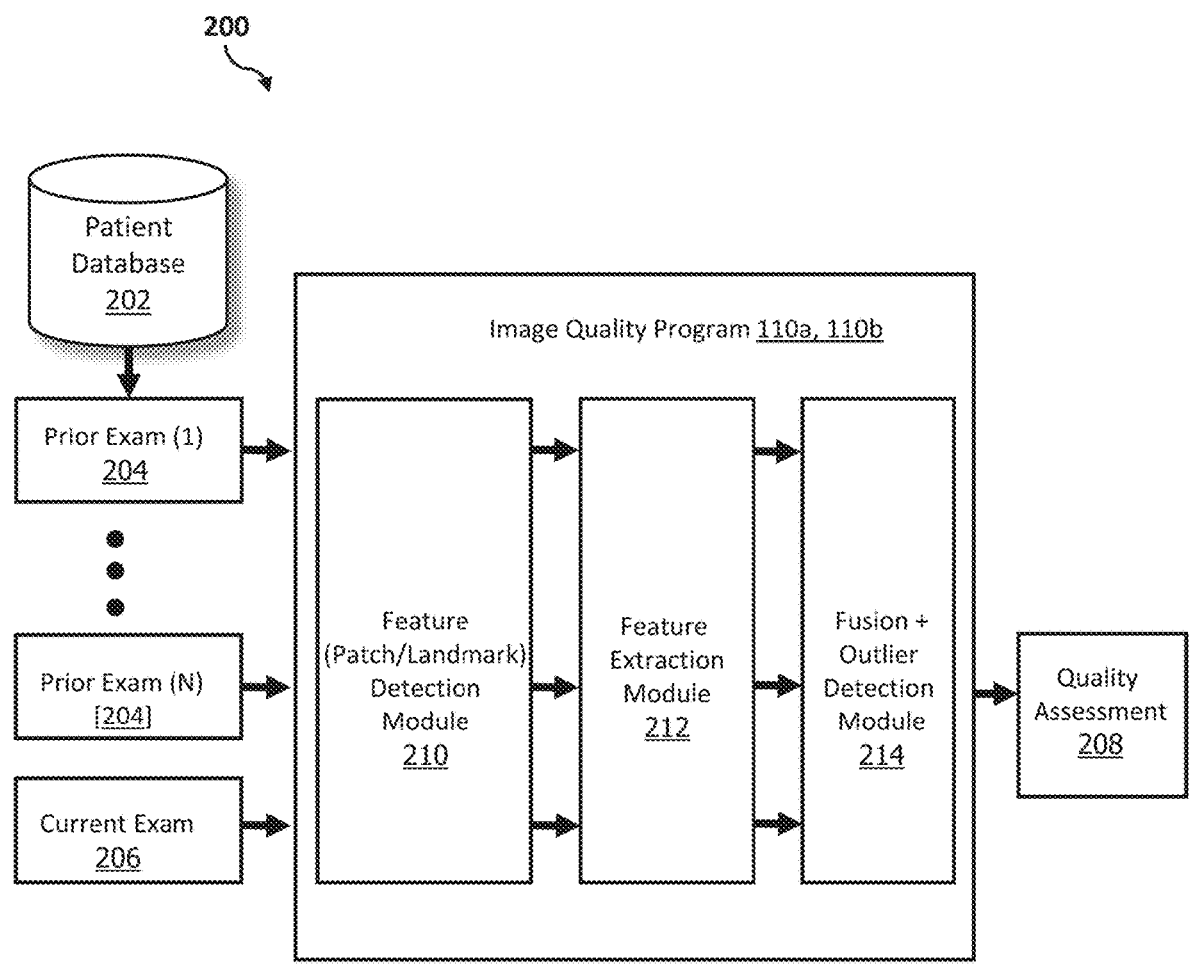
FIG. 2 is a block diagram of a quality assessment system according to at least one embodiment.

Referring now to FIG. 2, a block diagram illustrating a quality assessment system 200 according to at least one embodiment is depicted.

According to one embodiment, the quality assessment system 200 may be provided in the networked computer environment 100 and may be implemented on one or more client computers 102 and/or one or more server computers 112 to automatically evaluate image quality of medical images to determine whether the image quality is sufficient to enable the use of the medical images for diagnostic interpretations.

In one embodiment, the quality assessment system 200 may be incorporated with or included as a component in a computer-aided diagnosis (CAD) device operating autonomously to analyze medical images and provide diagnostic interpretations thereof. It is contemplated that the quality assessment system 200 may be applied to analyze the quality of any medical image. However, for the purposes of example, the quality assessment system 200 will be described with reference to mammogram medical images (e.g., radiographs).

In some instances, the image quality of medical images acquired from a patient may be influenced by the positioning of the patient relative to an imaging device (e.g., X-ray device, Magnetic Resonance Imaging (MRI) device). However, given the variations in patient anatomies, habitus (i.e., physique), and mobility-levels, which may impact the positioning of the patient relative to the imaging device and the ability of the imaging device to accommodate to the patient, a one-size-fits-all image quality standard may not be appropriate for all patients. Rather, it may be more appropriate and clinically useful to determine the image quality of medical images in a patient-specific basis, by leveraging data available from prior exams for each specific patient.

Accordingly, as further detailed below, the quality assessment system 200 may use prior medical images (e.g., from one or more prior exams) of a given patient to determine one or more characteristics of the given patient and define a patient-specific image quality threshold. Based on the patient-specific image quality threshold (e.g., from characteristics determined from the prior exams), the quality assessment system 200 may then determine if a current medical image (e.g., from a current exam) acquired from the given patient includes image quality issues requiring the imaging procedure to be repeated (e.g., quality assessment of current exam is lower than the patient-specific image quality threshold).

According to one embodiment, the quality assessment system 200 may generally include an image quality program 110a, 110b and a patient database 202. In one embodiment, the patient database 202 may include one or more prior exams 204 and one or more current exams 206 associated with a patient. In one embodiment, the quality assessment system 200 may implement the image quality program 110a, 110b to output a quality assessment 208 of the current exam 206 (e.g., current quality assessment) based on an input of the prior exams 204 and the current exam 206.

The image quality program 110a, 110b may include a single computer program or multiple program modules or sets of instructions being executed by the processor of the client computer 102/server computer 112. The image quality program 110a, 110b may include routines, objects, components, logic, data structures, and so on that may perform particular tasks or implement particular abstract data types. The image quality program 110a, 110b may be practiced in distributed cloud computing environments where tasks are performed by remote processing devices that may be linked through the communication network 116. In one embodiment, the multiple program modules of the image quality program 110a, 110b may include, for example, a feature detection module 210, a feature extraction module 212, and a fusion and outlier detection module 214.

The image quality program 110a, 110b may provide a workflow (e.g., events, tasks, or instructions that may be executed by the processor of the client computer 102/server computer 112) to enable a user to access the prior exams 204 and the current exam 206 stored in the patient database 202, and calculate a first or prior set of quality measurements based on the prior exams 204 and a second or current set of quality measurements based on the current exam 206. The image quality program 110a, 110b may then enable the user to compare the prior set of quality measurements with the current set of quality measurements to determine if the current quality assessment of the current exam 206 is lower than a patient-specific image quality threshold based on the quality assessment of the prior exams 204. If the image quality program 110a, 110b determines that the quality assessment of the current exam 206 is not lower than the patient-specific image quality threshold, the image quality program 110a, 110b may automatically register a positive quality assessment for the current exam 206 and maintain the current exam 206 for processing by a CAD device. However, if the image quality program 110*a*, 110*b* determines that the quality assessment of the current exam 206 is lower than the patient-specific image quality threshold, the image quality program 110*a*, 110*b* may automatically register a negative quality assessment for the current exam 206 and flag the current exam 206 as including low image quality.

According to one embodiment, the patient database 202 may be implemented as a picture archiving and communication system (PACS) for storing the medical images (e.g., electronic images) acquired during the prior exams 204 and current exam 206 using a variety of imaging device types, such as, for example, computed tomography, MRI, ultrasound, X-ray, fluoroscopy, angiography, and mammography. In one embodiment, the medical images may be formatted in the universal Digital Imaging and Communications in Medicine (DICOM) format. In one embodiment, the medical images may include embedded patient-identification labels and other tags describing the images (e.g., anatomical view).

In one embodiment, the patient database 202 may archive the prior exams 204 for further processing (e.g., via CAD device) and referencing. In one embodiment, the patient database 202 may temporarily store the current exam 206 during the quality assessment process and may delete the current exam 206 if the current exam is flagged as including low image quality. If the current exam 206 is determined to include good or sufficient image quality, the patient database 202 may archive the current exam 206 with the associated prior exams 204. In at least one embodiment, the patient database 202 may be stored in or implemented as part of the data storage device 106 of the client computer 102 or the database 114 of the server computer 112. In another embodiment, the patient database 202 may be stored remotely in a cloud computing environment.

According to one embodiment, the image quality program 110*a*, 110*b* may include the feature detection module 210. The image quality program 110*a*, 110*b* may implement the feature detection module 210 to detect a set of features in the medical image from which a set of feature attributes may be extracted to measure the quality of the medical image. In one embodiment the feature detection module 210 may use one or more computer vision algorithms (e.g., image segmentation, object detection) to detect the set of features in the medical image. In one embodiment, the set of features may include one or more anatomical landmarks which may indicate that all required anatomical tissue is visible and properly positioned the medical image. In one embodiment, the set of features may also include one or more patches which may be analyzed to detect blur or other artifacts that may result in low quality images. In another embodiment, the set of features may also include one or more edges which may indicate a boundary between two image regions of interest.

Figure 3:
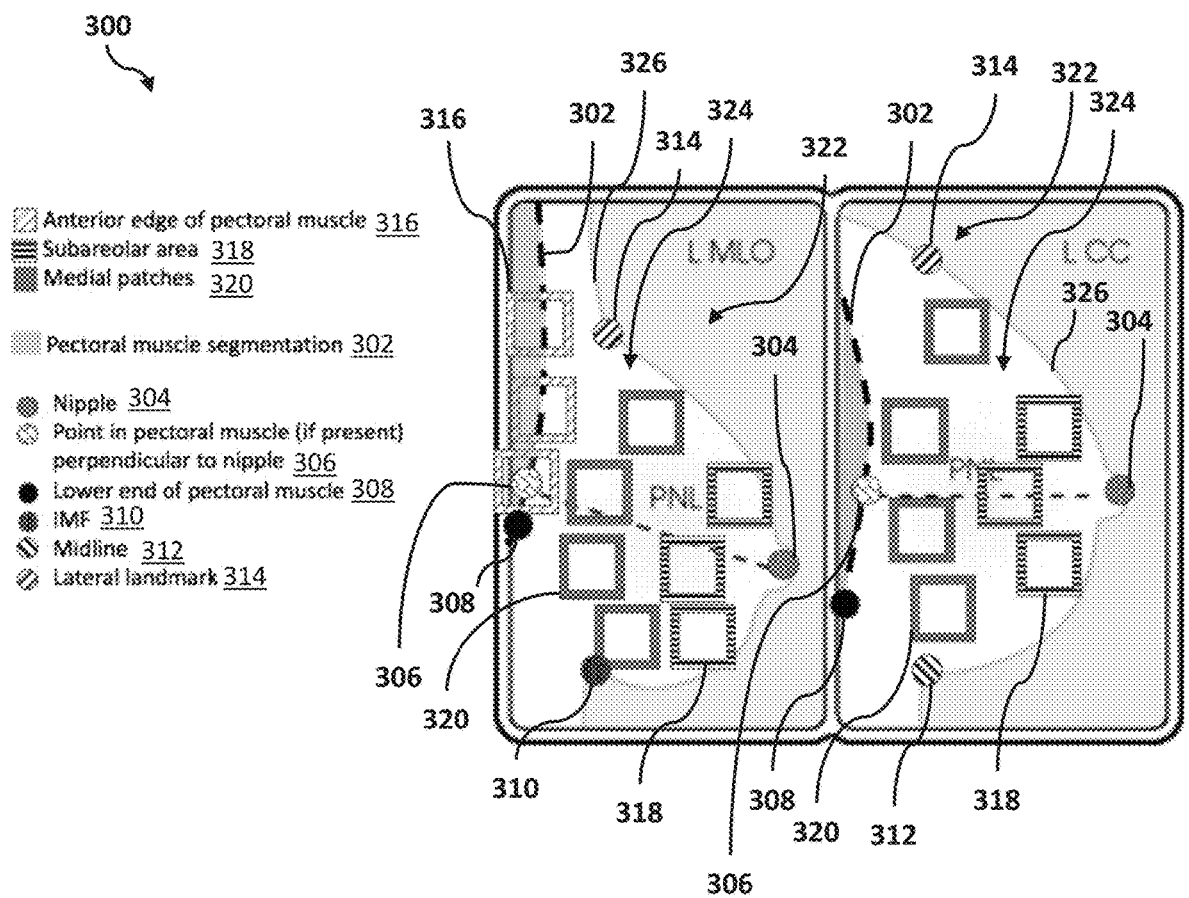
FIG. 3 is a block diagram illustrating an exemplary aspect of the quality assessment system according to at least one embodiment.

Referring now to FIG. 3, a block diagram illustrating an exemplary set of mammographic image features 300 according to at least one embodiment is depicted.

Mammogram exams typically include two projections: a mediolateral oblique (MLO) view and a craniocaudal (CC) view for each of the left breast (e.g., L MLO; L CC) and the right breast (e.g., R MLO; R CC). According to one embodiment, the feature detection module 210 may be trained to detect the set of mammographic image features 300 associated with each projection as illustrated in FIG. 3.

In one embodiment, the set of mammographic image features 300 may include anatomical landmarks associated with positioning of the patient to achieve maximum tissue visualization for clinical image analysis of the mammographic image. Specifically, the set of mammographic image features 300 may include a pectoral muscle segmentation 302, a nipple 304, a point in the pectoral muscle perpendicular to the nipple 306, a lower end of pectoral muscle 308, an inframammary fold (IMF) 310, a midline 312, and a lateral landmark 314. In another embodiment, the set of mammographic image features 300 may also include patches which may serve as optimal locations for detecting blur and artifacts in the mammographic image. Specifically, the set of mammographic image features 300 may include one or more anterior edge of pectoral muscle patches 316, one or more sub-areolar area patches 318, and one or more medial patches 320.

According to one embodiment, the feature detection module 210 may detect the pectoral muscle segmentation 302 by first dividing the mammographic image into a background region 322 and a breast region 324. The feature detection module 210 may implement a thresholding method to convert the mammographic image into a binary image where each image pixel with a pixel intensity that is less than a threshold intensity may be replaced with a black pixel (e.g., 1-pixel) and each image pixel with a pixel intensity that is more than a threshold intensity may be replaced with a white pixel (e.g., 0-pixel). Given the difference in pixel intensities between the background region 311 and the breast region 324, the thresholding method may be used to convert the pixels in the breast region to white pixels and convert the pixels in the background region 322 to black pixels. In one embodiment, the threshold may be solved in an image domain and on different transformed versions of the mammographic image. In one embodiment, the feature detection module 210 may apply a series of morphological operations on the binary image to identify the shape of the breast region 324 and a breast boundary 326 between the background region 322 and the breast region 324. In one embodiment, the morphological operation may include a dilation process (e.g., expand a connected set of 1-pixels in the binary image), an erosion process (e.g., a connected set of 1-pixels in the binary image), an opening process (e.g., compound of erosion followed by dilation), and a closing process (e.g., compound of dilation followed by erosion). By applying the opening and closing processes of the morphological operations, the feature detection module 210 may identify the largest connected components in the binary image, such as, for example, the breast region 324 and the breast boundary 326. In one embodiment, after the breast region 324 is detected, the feature detection module 210 may identify the pectoral muscle segmentation 302 by selecting an initial location of the pectoral muscle (e.g., seed points) and implementing a region growing algorithm to analyze the pixels neighboring the seed points to determine whether the pixels should be added to the initial location based on one or more criterion (e.g., intensity, texture, color).

According to one embodiment, after detecting the pectoral muscle segmentation 302 and the breast boundary 326, the feature detection module 210 may detect the remaining set of mammographic image features 300 by determining the location of the feature with reference to the pectoral muscle segmentation 302, the breast boundary 326, and the nipple.

In at least one embodiment, if the mammographic image includes scanning artifacts, such as, patient labels or other radio-opaque markers (e.g., needle guidewire, biopsy clip) the feature detection module 210 may apply the morphological operations (e.g., opening and closing process) to identify and eliminate the connected components representing the artifacts from the image.

With continued reference to FIG. 2, once the set of features 300 have been detected by the feature detection module 210, the image quality program 110a, 110b may implement the feature extraction module 212 to obtain a set of quality measurements from the set of features 300 detected by the feature detection module 210.

According to one embodiment, the feature extraction module 212 may calculate the set of quality measurements in both the prior exams 204 (e.g., first or prior set of quality measurements) and the current exam 206 (e.g., second or current set of quality measurements). In one embodiment, the first set of quality measurements based on the prior exams 204 may indicate one or more characteristics of a given patient, which may serve as the patient-specific image quality threshold when determining the quality assessment of the current exam 206 and future exams.

According to one embodiment, the set of quality measurements may include, for example, a posterior nipple line (PNL) length (i.e., perpendicular line from nipple to a point on the pectoral muscle, where the PNL measurement of the CC projection and the MLO projection should be within one centimeter); a determination of whether the nipple is in profile; a determination of whether the pectoral muscle is missing from the image; a determination of whether the nipple is centered (in the L CC and R CC view); a pectoral muscle to breast length ratio; a pectoral muscle to breast area ratio; a determination of whether the IMF is present; the IMF length; and a determination of whether there is blur in the image.

As noted above, the first set of quality measurements calculated based on the prior exams 204 may serve as the patient-specific image quality threshold when determining the quality assessment of the current exam 206. According to one embodiment, the image quality program 110a, 110b may implement the fusion and outlier detection module 214 to compare the second set of quality measurements calculated based on the current exam 206 with the patient-specific image quality threshold defined by the prior exams 204 to determine a patient-specific quality assessment of the current exam 206. In one embodiment, the fusion and outlier detection module 214 may compress the multi-dimensional data (e.g., first set of quality measurements) calculated from the prior exams 204 and compare the compressed multi-dimensional data with the second set of quality measurements based on the current exam 206 to detect or classify outliers in the current exam 206. For example, the fusion and outlier detection module 214 may calculate that in five prior exams 204, the PNL length measurements in the CC projection and the MLO projection fall within a range of one centimeter. Then, if the fusion and outlier detection module 214 calculates that the PNL length measurements in the CC projection and the MLO projection of the current exam 206 differ by more than one centimeter, the fusion and outlier detection module 214 may detect the PNL length as an outlier in the current exam 206.

According to one embodiment, the image quality program 110a, 110b may return the quality assessment 208 of the current exam 206 based on the comparison performed by the fusion and outlier detection module 214. In one embodiment, the prior exams 204 may indicate a baseline (e.g., high) quality for the given patient. The prior exams 204 may establish whether low quality in the current exam 206 may be caused by the imaging procedure (in which case the exam may be repeated) or by the patient anatomy, habitus, or reduced mobility. As such, if the quality assessment of the current exam 206 is significantly lower than the prior exams 204, the image quality program 110a, 110b may automatically register a negative quality assessment for the current exam 206 and return the quality assessment 208 of the current exam 206 as indicating the negative quality assessment.

Figure 4:
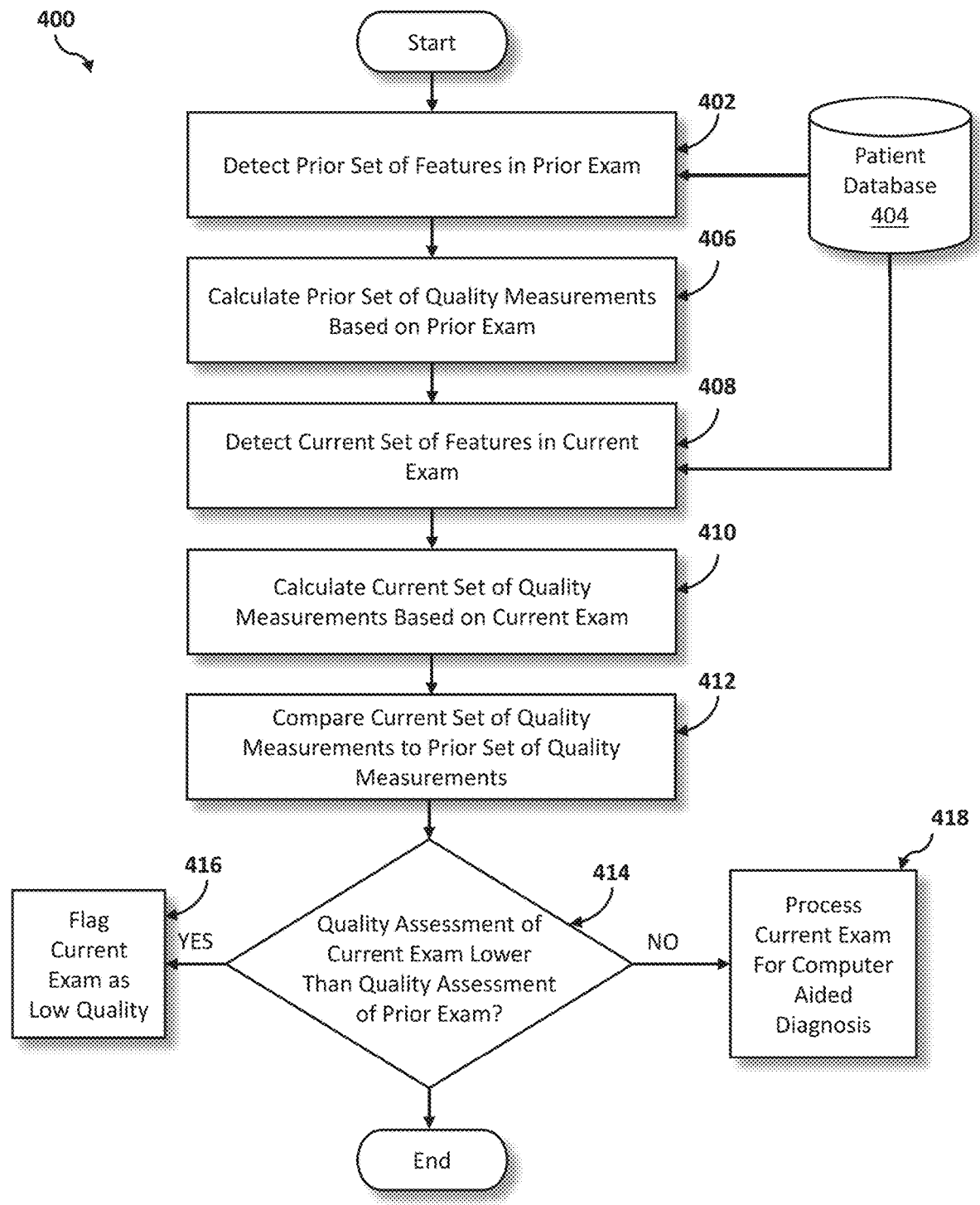
FIG. 4 is an operational flowchart illustrating a process for quality assessment according to at least one embodiment.
Figure 5:
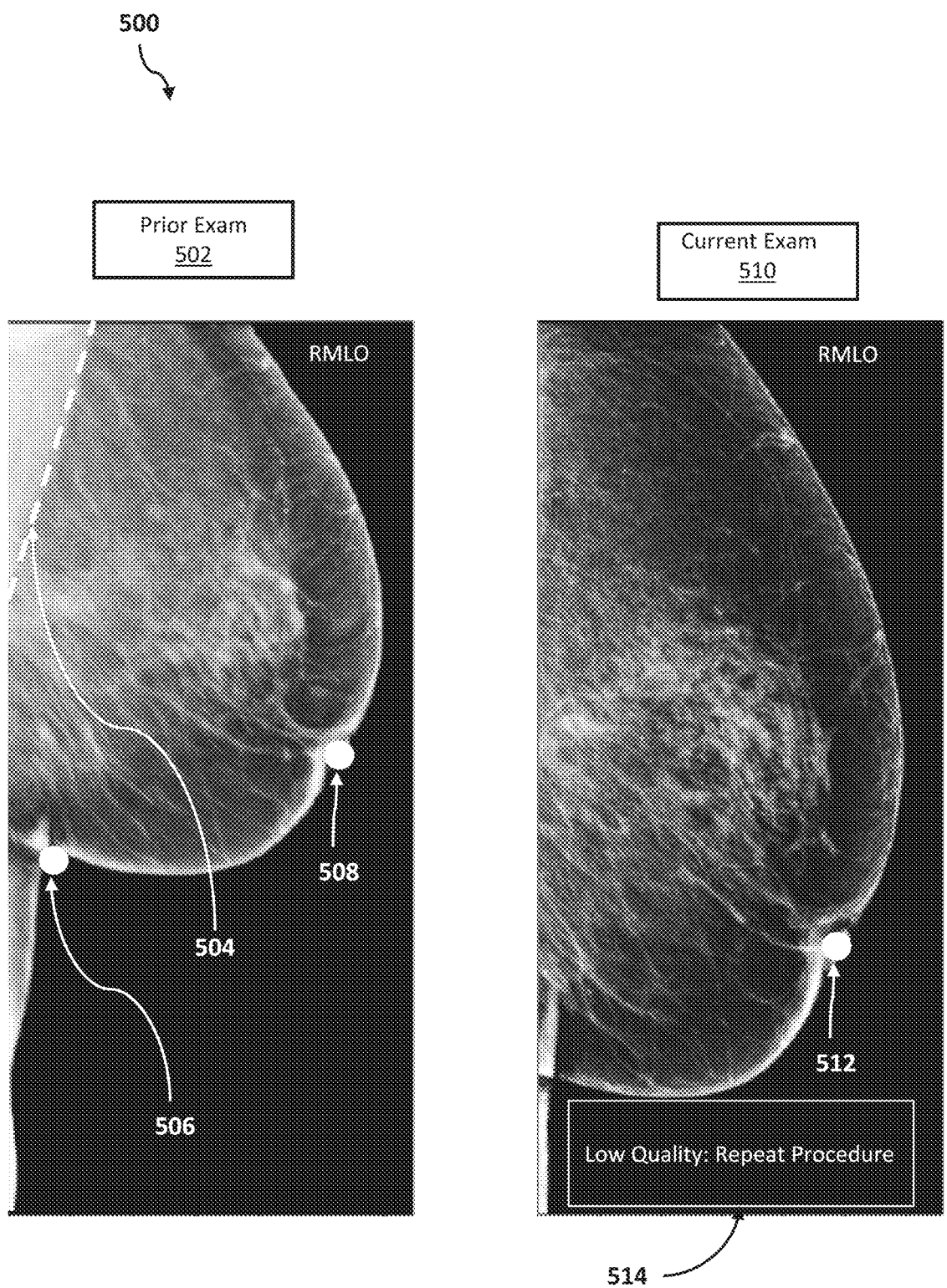
FIG. 5 is an exemplary illustration of the process for quality assessment according to at least one embodiment.

Referring now to FIG. 4, an operational flowchart illustrating an exemplary quality assessment process 400 used by the image quality program 110a and 110b, as described in connection to FIGS. 2 and 3, according to at least one embodiment is depicted. Referring also to FIG. 5, an exemplary illustration of a quality assessment process 500 used by the image quality program 110a and 110b, as described in connection to FIGS. 2 and 3, according to at least one embodiment is depicted.

At 402, a prior set of features is detected in a prior exam. According to one embodiment, the image quality program 110a, 110b running on the client computer 102 or the server computer 112 may receive (e.g., via communication network 116) the prior exam (e.g., prior exam 204) from a patient database 404, similar to the previously described patient database 202. Then, the image quality program 110a, 110b may implement the feature detection module 210 to detect the prior set of features in the prior exam. As previously described, the prior set of features may include anatomical landmarks which may indicate proper positioning of the tissue in the medical image. In another embodiment, the prior set of features may also include patches which may be analyzed to detect blur or other artifacts which may result in low quality images.

In one example, with reference to the exemplary quality assessment process 500 depicted in FIG. 5, the image quality program 110a, 110b receives, via communication network 116, a prior exam 502 from the patient database (e.g., patient database 202; patient database 404). Then, the image quality program 110a, 110b may implement the feature detection module 210 to detect the set of features 300 in the prior exam 502, as previously described with reference to FIG. 3. As shown in FIG. 5, the feature detection module 210 detects a pectoral muscle segmentation 504, an IMF landmark 506, and a nipple landmark 508 in the prior exam 502.

Then, at 406, a prior set of quality measurements is calculated based on the prior exam. After the feature detection module 210 detects the prior set of features in the prior exam, the image quality program 110a, 110b may implement the feature extraction module 212 to calculate the prior set of quality measurements from the detected prior set of features. As previously described in connection with FIGS. 2 and 3, the prior set of quality measurements based on the prior exam 204 may indicate one or more characteristics of a given patient. According to one embodiment, the prior set of quality measurements may define a patient-specific image quality threshold, as previously described.

Continuing with the previous example, the image quality program 110a, 110b implements the feature extraction module 212 to calculate the prior set of quality measurements from the detected prior set of features in the prior exam 502, as previously described. Based on the detected pectoral muscle segmentation 504, the IMF landmark 506, and the nipple landmark 508, the feature extraction module 212 calculates that the pectoral muscle, the IMF, and the nipple are visualized in the prior exam 502.

Then, at 408, a current set of features is detected in a current exam. According to one embodiment, the image quality program 110a, 110b may receive (e.g., via communication network 116) the current exam (e.g., current exam 206) from the patient database 404, similar to the previously described patient database 202. Then, the image quality program 110*a*, 110*b* may implement the feature detection module 210 to detect the current set of features in the current exam in a manner similar to detecting the first set of features in the prior exam.

Continuing with the previous example, the image quality program 110*a*, 110*b* receives, via communication network 116, a current exam 510 from the patient database (e.g., patient database 202; patient database 404). Then, the image quality program 110*a*, 110*b* may implement the feature detection module 210 to detect the set of features 300 in the current exam 510, as previously described with reference to FIG. 3. As shown in FIG. 5, the feature detection module 210 detects a nipple landmark 512 in the current exam 510.

Then, at 410, a current set of quality measurements is calculated based on the current exam. After the feature detection module 210 detects the current set of features in the current exam, the image quality program 110*a*, 110*b* may implement the feature extraction module 212 to calculate the current set of quality measurements from the detected second set of features, as previously described.

Continuing with the previous example, the image quality program 110*a*, 110*b* implements the feature extraction module 212 to calculate the current set of quality measurements from the detected current set of features in the current exam 510, as previously described. Based on the detected the nipple landmark 512, the feature extraction module 212 calculates that the nipple is visualized in the current exam 510.

Then at 412, the current set of quality measurements is compared to the prior set of quality measurements. According to one embodiment, the image quality program 110*a*, 110*b* may implement the fusion and outlier detection module 214 to compare the current set of quality measurements calculated based on the current exam with the prior set of quality measurements from the prior exams to determine a patient-specific quality assessment of the current exam. According to one embodiment, the image quality program 110*a*, 110*b* may compare the current set of quality measurements calculated based on the current exam with the patient-specific image quality threshold defined by the prior exams.

Continuing with the previous example, the image quality program 110*a*, 110*b* implements the fusion and outlier detection module 214 the current set of quality measurements obtained from the current exam 510 with the prior set of quality measurements obtained from the prior exam 502. The current set of quality measurements indicate that the nipple (nipple landmark 512) is visualized in the current exam 510. The prior set of quality measurements indicate that the pectoral muscle, the IMF, and the nipple are visualized in the prior exam 502. Based on the comparison between the current exam 510 and the prior exam 502, the fusion and outlier detection module 214 determines that the pectoral muscle and the IMF are missing from (e.g., not visualized) in the current exam 510. In one embodiment, the patient-specific image quality threshold defined by the prior exam 502 indicates that the pectoral muscle, the IMF, and the nipple are capable of being visualized. As such, the current set of quality measurements in the current exam 510 fall below the patient-specific image quality threshold defined by the prior exam 502.

Thereafter in 414, the image quality program 110*a*, 110*b* determines if a quality assessment of the current exam (e.g., current quality assessment) is lower than a quality assessment of the prior exam (e.g., prior quality assessment). According to one embodiment, the image quality program 110*a*, 110*b* may return a quality assessment (e.g., quality assessment 208) of the current exam 206 based on the comparison performed by the fusion and outlier detection module 214, as previously described.

If at 414, the image quality program 110*a*, 110*b* determines that the quality assessment of the current exam (e.g., second quality assessment) is lower than the quality assessment of the prior exam (e.g., first quality assessment), then at 416, the image quality program 110*a*, 110*b* flags the current exam as low quality. In one embodiment, the image quality program 110*a*, 110*b* may automatically register a negative quality assessment for the current exam. According to one embodiment, the image quality program 110*a*, 110*b* may transmit a notification via a graphical user interface (GUI) to indicate the flagged low quality of the current exam. In another embodiment, the image quality program 110*a*, 110*b* may transmit an instruction via a GUI notification indicating that the imaging procedure should be repeated. In another embodiment, the image quality program 110*a*, 110*b* may delete the current exam from the patient database 404.

However, if at 414, the image quality program 110*a*, 110*b* determines that the current quality assessment of the current exam is not lower than the prior quality assessment of the prior exam, then at 418, the image quality program 110*a*, 110*b* processes the current exam for CAD analysis, as previously described.

Continuing with the previous example, after the fusion and outlier detection module 214 determines that the pectoral muscle and the IMF are not visualized in the current exam 510, the image quality program 110*a*, 110*b* determines that the second quality assessment of the current exam is lower than the patient-specific image quality threshold defined the first quality assessment of the prior exam. Thereafter, the image quality program 110*a*, 110*b* transmits a notification 514 via the GUI of the image quality program 110*a*, 110*b* indicating that the current exam 510 is low quality (based on the patient-specific image quality threshold defined by prior exam 502) and that the imaging procedure should be repeated.

The functionality of a computer may be improved by the image quality program 110*a*, 110*b* because the image quality program 110*a*, 110*b* may automatically determine whether a current image includes sufficient quality for diagnostic interpretation by a CAD device and may determine the quality of the current image in a patient-by-patient basis, by leveraging data available from prior images for each patient.

It may be appreciated that FIGS. 2 to 5 provide only an illustration of one embodiment and does not imply any limitations with regard to how different embodiments may be implemented. Many modifications to the depicted embodiment(s) may be made based on design and implementation requirements.

Figure 6:
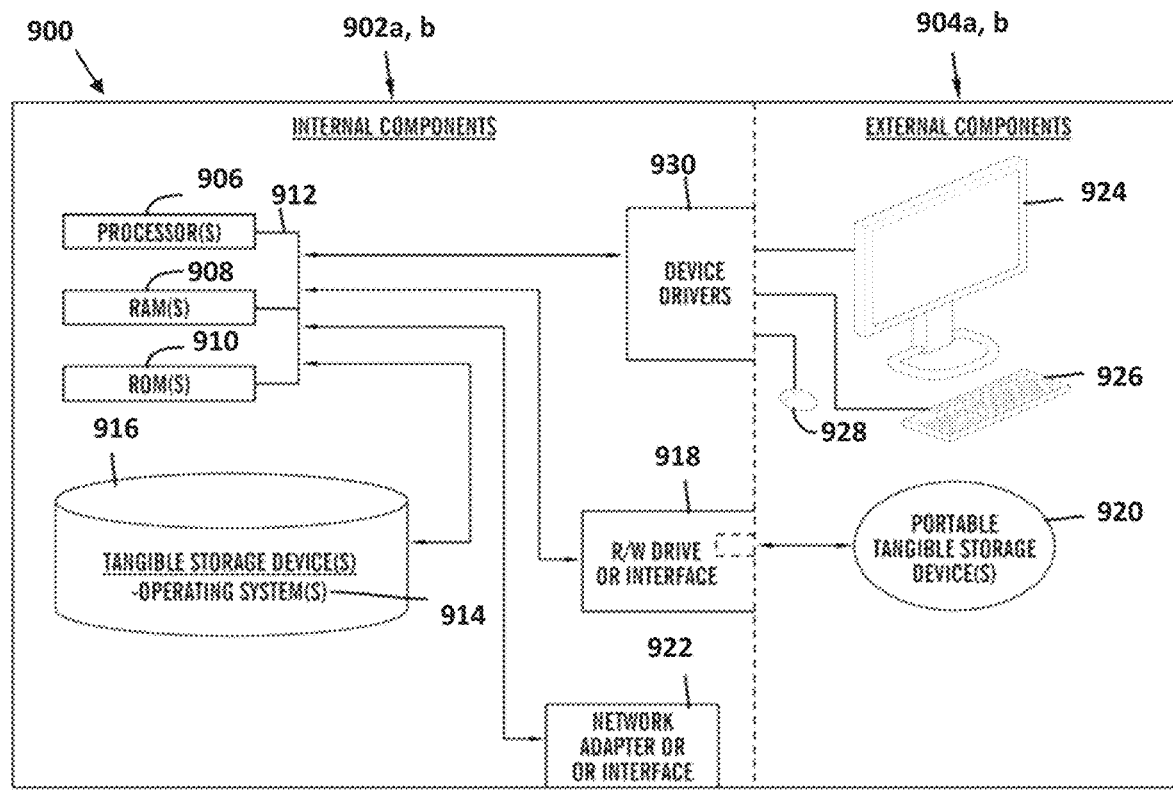
FIG. 6 is a block diagram of internal and external components of computers and servers depicted in FIG. 1 according to at least one embodiment.

FIG. 6 is a block diagram 900 of internal and external components of computers depicted in FIG. 1 in accordance with an illustrative embodiment of the present invention. It should be appreciated that FIG. 6 provides only an illustration of one implementation and does not imply any limitations with regard to the environments in which different embodiments may be implemented. Many modifications to the depicted environments may be made based on design and implementation requirements.

Data processing system 902, 904 is representative of any electronic device capable of executing machine-readable program instructions. Data processing system 902, 904 may be representative of a smart phone, a computer system, PDA, or other electronic devices. Examples of computing systems, environments, and/or configurations that may represented by data processing system 902, 904 include, but are not limited to, personal computer systems, server computer systems, thin clients, thick clients, hand-held or laptop devices, multiprocessor systems, microprocessor-based systems, network PCs, minicomputer systems, and distributed cloud computing environments that include any of the above systems or devices.

User client computer 102 and network server 112 may include respective sets of internal components 902 a, b and external components 904 a, b illustrated in FIG. 6. Each of the sets of internal components 902 a, b includes one or more processors 906, one or more computer-readable RAMs 908 and one or more computer-readable ROMs 910 on one or more buses 912, and one or more operating systems 914 and one or more computer-readable tangible storage devices 916. The one or more operating systems 914, the software program 108, and the image quality program 110a in client computer 102, and the image quality program 110b in network server 112, may be stored on one or more computer-readable tangible storage devices 916 for execution by one or more processors 906 via one or more RAMs 908 (which typically include cache memory). In the embodiment illustrated in FIG. 6, each of the computer-readable tangible storage devices 916 is a magnetic disk storage device of an internal hard drive. Alternatively, each of the computer-readable tangible storage devices 916 is a semiconductor storage device such as ROM 910, EPROM, flash memory or any other computer-readable tangible storage device that can store a computer program and digital information.

Each set of internal components 902 a, b also includes a R/W drive or interface 918 to read from and write to one or more portable computer-readable tangible storage devices 920 such as a CD-ROM, DVD, memory stick, magnetic tape, magnetic disk, optical disk or semiconductor storage device. A software program, such as the software program 108 and the image quality program 110a and 110b can be stored on one or more of the respective portable computer-readable tangible storage devices 920, read via the respective R/W drive or interface 918 and loaded into the respective hard drive 916.

Each set of internal components 902 a, b may also include network adapters (or switch port cards) or interfaces 922 such as a TCP/IP adapter cards, wireless wi-fi interface cards, or 3G or 4G wireless interface cards or other wired or wireless communication links. The software program 108 and the image quality program 110a in client computer 102 and the image quality program 110b in network server computer 112 can be downloaded from an external computer (e.g., server) via a network (for example, the Internet, a local area network or other, wide area network) and respective network adapters or interfaces 922. From the network adapters (or switch port adaptors) or interfaces 922, the software program 108 and the image quality program 110a in client computer 102 and the image quality program 110b in network server computer 112 are loaded into the respective hard drive 916. The network may comprise copper wires, optical fibers, wireless transmission, routers, firewalls, switches, gateway computers and/or edge servers.

Each of the sets of external components 904 a, b can include a computer display monitor 924, a keyboard 926, and a computer mouse 928. External components 904 a, b can also include touch screens, virtual keyboards, touch pads, pointing devices, and other human interface devices. Each of the sets of internal components 902 a, b also includes device drivers 930 to interface to computer display monitor 924, keyboard 926 and computer mouse 928. The device drivers 930, R/W drive or interface 918 and network adapter or interface 922 comprise hardware and software (stored in storage device 916 and/or ROM 910).

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 7:
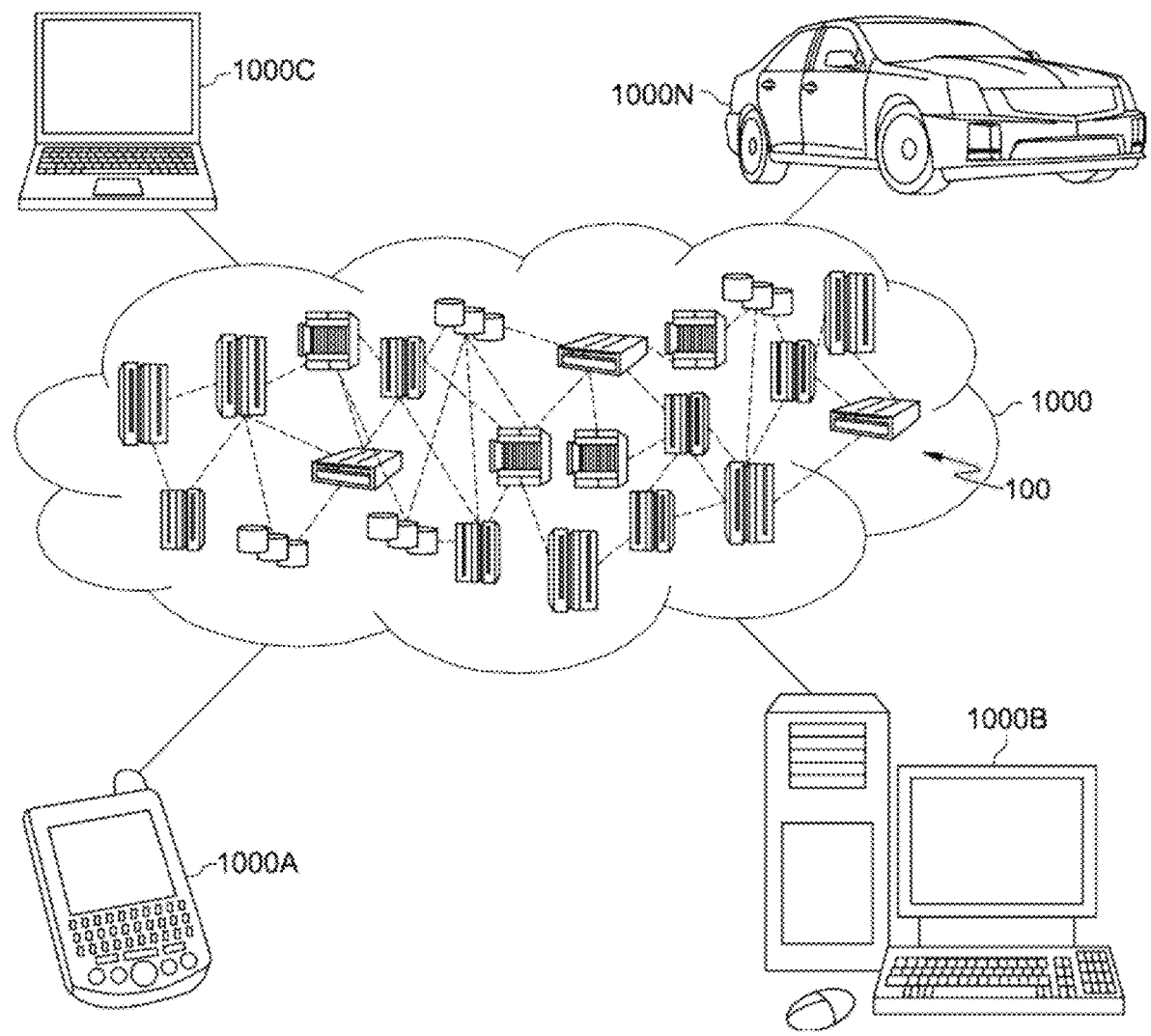
FIG. 7 is a block diagram of an illustrative cloud computing environment including the computer system depicted in FIG. 1, in accordance with an embodiment of the present disclosure.

Referring now to FIG. 7, illustrative cloud computing environment 1000 is depicted. As shown, cloud computing environment 1000 comprises one or more cloud computing nodes 100 with which local computing devices used by cloud consumers, such as, for example, personal digital assistant (PDA) or cellular telephone 1000A, desktop computer 1000B, laptop computer 1000C, and/or automobile computer system 1000N may communicate. Nodes 100 may communicate with one another. They may be grouped (not shown) physically or virtually, in one or more networks, such as Private, Community, Public, or Hybrid clouds as described hereinabove, or a combination thereof. This allows cloud computing environment 1000 to offer infrastructure, platforms and/or software as services for which a cloud consumer does not need to maintain resources on a local computing device. It is understood that the types of computing devices 1000A-N shown in FIG. 7 are intended to be illustrative only and that computing nodes 100 and cloud computing environment 1000 can communicate with any type of computerized device over any type of network and/or network addressable connection (e.g., using a web browser).

Figure 8:
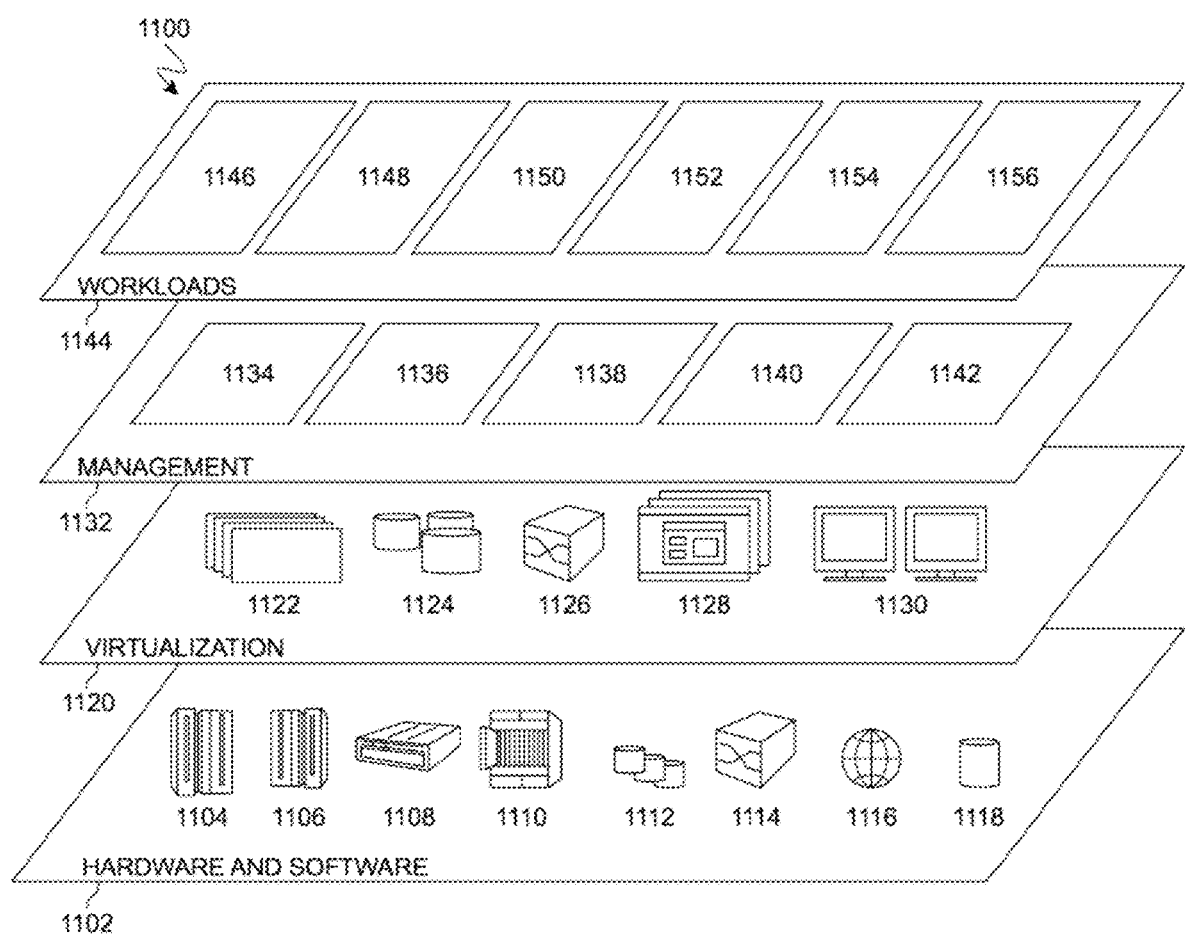
FIG. 8 is a block diagram of functional layers of the illustrative cloud computing environment of FIG. 7, in accordance with an embodiment of the present disclosure.

Referring now to FIG. 8, a set of functional abstraction layers 1100 provided by cloud computing environment 1000 is shown. It should be understood in advance that the components, layers, and functions shown in FIG. 8 are intended to be illustrative only and embodiments of the invention are not limited thereto. As depicted, the following layers and corresponding functions are provided:

Hardware and software layer 1102 includes hardware and software components. Examples of hardware components include: mainframes 1104; RISC (Reduced Instruction Set Computer) architecture based servers 1106; servers 1108; blade servers 1110; storage devices 1112; and networks and networking components 1114. In some embodiments, software components include network application server software 1116 and database software 1118.

Virtualization layer 1120 provides an abstraction layer from which the following examples of virtual entities may be provided: virtual servers 1122; virtual storage 1124; virtual networks 1126, including virtual private networks; virtual applications and operating systems 1128; and virtual clients 1130.

In one example, management layer 1132 may provide the functions described below. Resource provisioning 1134 provides dynamic procurement of computing resources and other resources that are utilized to perform tasks within the cloud computing environment. Metering and Pricing 1136 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 1138 provides access to the cloud computing environment for consumers and system administrators. Service level management 1140 provides cloud computing resource allocation and management such that required service levels are met. Service Level Agreement (SLA) planning and fulfillment 1142 provide pre-arrangement for, and procurement of, cloud computing resources for which a future requirement is anticipated in accordance with an SLA.

Workloads layer 1144 provides examples of functionality for which the cloud computing environment may be utilized. Examples of workloads and functions which may be provided from this layer include: mapping and navigation 1146; software development and lifecycle management 1148; virtual classroom education delivery 1150; data analytics processing 1152; transaction processing 1154; and quality assessment 1156. An image quality program 110a, 110b provides a way to define a patient-specific image quality threshold based on prior exams conducted on a given patient and determine if a current exam conducted on the given patient meets the patient-specific image quality threshold.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer-implemented method comprising:
   detecting a prior set of features in at least one prior exam associated with a patient, wherein the detected prior set of features in at least one prior exam includes at least one anatomical landmark associated with the patient;
   calculating a prior set of quality measurements for the at least one prior exam based on the detected prior set of features, wherein the at least one anatomical landmark detected in the at least one prior exam indicates proper positioning of a tissue of the patient in the at least one prior exam;

recording a patient-specific image quality threshold based on the calculated prior set of quality measurements for the at least one prior exam, wherein the recorded patient-specific image quality threshold indicates that the at least one prior exam includes sufficient quality for diagnostic interpretation by a computer-aided diagnosis (CAD) device;

detecting a current set of features in a current exam associated with the patient;

calculating a current set of quality measurements for the current exam based on the detected current set of features; and in response to determining that the at least one anatomical landmark detected in the at least one prior exam is not included in the detected current set of features, such that the calculated current set of quality measurements for the current exam is below the recorded patient-specific image quality threshold defined by the at least one prior exam associated with the patient, automatically registering a negative quality assessment for the current exam associated with the patient.

2. The method of claim 1, further comprising:
in response to automatically registering the negative quality assessment for the current exam associated with the patient, transmitting an instruction via a graphical user interface (GUI) notification to repeat the current exam.

3. The method of claim 1, further comprising:
in response to determining that the calculated current set of quality measurements for the current exam meets the patient-specific image quality threshold defined by the at least one prior exam associated with the patient, automatically registering a positive quality assessment for the current exam associated with the patient.

4. The method of claim 2, wherein the detected current set of features in the current exam and the detected prior set of features in the at least one prior exam are selected from the group consisting of: an anterior edge of a pectoral muscle patch, a sub-areolar area patch, a medial patch, a pectoral muscle segmentation, a nipple, a point in pectoral muscle perpendicular to the nipple, a lower end of the pectoral muscle, an inframammary fold (IMF), a midline, and a lateral landmark.

5. The method of claim 2, wherein the calculated current set of quality measurements for the current exam and the calculated prior set of quality measurements for the at least one prior exam are selected from the group consisting of: a posterior nipple line (PNL) measurement, a nipple in profile determination, a missing pectoral muscle determination, a centered nipple determination, a pectoral muscle-to-breast length ratio, a pectoral muscle-to-breast area ratio, a determination of whether an IMF is present, an IMF length, and a blur determination.

6. The method of claim 3, further comprising:
in response to automatically registering the positive quality assessment for the current exam associated with the patient, determining that the current exam includes sufficient quality for diagnostic interpretation by the CAD device.

7. A computer system for case-adaptive image quality assessment, comprising:
one or more processors, one or more computer-readable memories, one or more computer-readable tangible storage media, and program instructions stored on at least one of the one or more computer-readable tangible storage media for execution by at least one of the one or more processors via at least one of the one or more memories, wherein the computer system is capable of performing a method comprising:

detecting a prior set of features in at least one prior exam associated with a patient, wherein the detected prior set of features in at least one prior exam includes at least one anatomical landmark associated with the patient;

calculating a prior set of quality measurements for the at least one prior exam based on the detected prior set of features, wherein the at least one anatomical landmark detected in the at least one prior exam indicates proper positioning of a tissue of the patient in the at least one prior exam;

recording a patient-specific image quality threshold based on the calculated prior set of quality measurements for the at least one prior exam, wherein the recorded patient-specific image quality threshold indicates that the at least one prior exam includes sufficient quality for diagnostic interpretation by a computer-aided diagnosis (CAD) device;

detecting a current set of features in a current exam associated with the patient;

calculating a current set of quality measurements for the current exam based on the detected current set of features; and in response to determining that the at least one anatomical landmark detected in the at least one prior exam is not included in the detected current set of features, such that the calculated current set of quality measurements for the current exam is below the recorded patient-specific image quality threshold defined by the at least one prior exam associated with the patient, automatically registering a negative quality assessment for the current exam associated with the patient.

8. The computer system of claim 7, further comprising:
in response to automatically registering the negative quality assessment for the current exam associated with the patient, transmitting an instruction via a graphical user interface (GUI) notification to repeat the current exam.

9. The computer system of claim 7, further comprising:
in response to determining that the calculated current set of quality measurements for the current exam meets the patient-specific image quality threshold defined by the at least one prior exam associated with the patient, automatically registering a positive quality assessment for the current exam associated with the patient.

10. The computer system of claim 8, wherein the detected current set of features in the current exam and the detected prior set of features in the at least one prior exam are selected from the group consisting of: an anterior edge of a pectoral muscle patch, a sub-areolar area patch, a medial patch, a pectoral muscle segmentation, a nipple, a point in pectoral muscle perpendicular to the nipple, a lower end of the pectoral muscle, an inframammary fold (IMF), a midline, and a lateral landmark.

11. The computer system of claim 8, wherein the calculated current set of quality measurements for the current exam and the calculated prior set of quality measurements for the at least one prior exam are selected from the group consisting of: a posterior nipple line (PNL) measurement, a nipple in profile determination, a missing pectoral muscle determination, a centered nipple determination, a pectoral muscle-to-breast length ratio, a pectoral muscle-to-breast area ratio, a determination of whether an IMF is present, an IMF length, and a blur determination.

12. The computer system of claim 9, further comprising:
in response to automatically registering the positive quality assessment for the current exam associated with the patient, determining that the current exam includes sufficient quality for diagnostic interpretation by the CAD device.

13. A computer program product for case-adaptive image quality assessment, the computer program product comprising a computer readable storage medium having program instructions embodied therewith, the program instructions executable by a processor to cause the processor to perform a method comprising:

detecting a prior set of features in at least one prior exam associated with a patient, wherein the detected prior set of features in at least one prior exam includes at least one anatomical landmark associated with the patient;

calculating a prior set of quality measurements for the at least one prior exam based on the detected prior set of features, wherein the at least one anatomical landmark detected in the at least one prior exam indicates proper positioning of a tissue of the patient in the at least one prior exam;

recording a patient-specific image quality threshold based on the calculated prior set of quality measurements for the at least one prior exam, wherein the recorded patient-specific image quality threshold indicates that the at least one prior exam includes sufficient quality for diagnostic interpretation by a computer-aided diagnosis (CAD) device;

detecting a current set of features in a current exam associated with the patient;

calculating a current set of quality measurements for the current exam based on the detected current set of features; and in response to determining that the at least one anatomical landmark detected in the at least one prior exam is not included in the detected current set of features, such that the calculated current set of quality measurements for the current exam is below the recorded patient-specific image quality threshold defined by the at least one prior exam associated with the patient, automatically registering a negative quality assessment for the current exam associated with the patient.

14. The computer program product of claim 13, further comprising:

in response to automatically registering the negative quality assessment for the current exam associated with the patient, transmitting an instruction via a graphical user interface (GUI) notification to repeat the current exam.

15. The computer program product of claim 13, further comprising:

in response to determining that the calculated current set of quality measurements for the current exam meets the patient-specific image quality threshold defined by the at least one prior exam associated with the patient, automatically registering a positive quality assessment for the current exam associated with the patient.

16. The computer program product of claim 14, wherein the detected current set of features in the current exam and the detected prior set of features in the at least one prior exam are selected from the group consisting of: an anterior edge of a pectoral muscle patch, a sub-areolar area patch, a medial patch, a pectoral muscle segmentation, a nipple, a point in pectoral muscle perpendicular to the nipple, a lower end of the pectoral muscle, an inframammary fold (IMF), a midline, and a lateral landmark.

17. The computer program product of claim 14, wherein the calculated current set of quality measurements for the current exam and the calculated prior set of quality measurements for the at least one prior exam are selected from the group consisting of: a posterior nipple line (PNL) measurement, a nipple in profile determination, a missing pectoral muscle determination, a centered nipple determination, a pectoral muscle-to-breast length ratio, a pectoral muscle-to-breast area ratio, a determination of whether an IMF is present, an IMF length, and a blur determination.

* * * * *